United States Patent [19]

Pieper

[11] Patent Number: 4,692,282
[45] Date of Patent: Sep. 8, 1987

[54] PHENYLTETRALINE-DIPHOSPHONIC ACIDS AND PROCESS FOR MAKING THEM

[75] Inventor: Werner Pieper, Kerpen, Fed. Rep. of Germany

[73] Assignee: Hoechst Aktiengesellschaft, Fed. Rep. of Germany

[21] Appl. No.: 859,123

[22] Filed: May 2, 1986

[30] Foreign Application Priority Data

May 18, 1985 [DE] Fed. Rep. of Germany ....... 3517969

[51] Int. Cl.$^4$ ................................................ C07F 9/38
[52] U.S. Cl. ............................................. 260/502.4 P
[58] Field of Search ................... 260/502.4 P, 502.4 D

[56] References Cited

FOREIGN PATENT DOCUMENTS 2455624  5/1976  Fed. Rep. of Germany ... 260/502.4 P

Primary Examiner—J. E. Evans
Attorney, Agent, or Firm—Connolly and Hutz

[57] ABSTRACT

Novel-1-phenyltetraline-1,4-diphosphonic acids of the formula

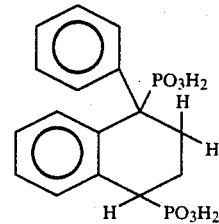

are made by reacting 1-phenylvinyl-1-phosphonic acids at temperatures of from 120°–210° C.

5 Claims, No Drawings

PHENYLTETRALINE-DIPHOSPHONIC ACIDS AND PROCESS FOR MAKING THEM

This present invention relates to diastereoisomeric α- and β-1-phenyltetraline-1,4-diphosphonic acids not described heretofore, and to a process for making them.

1phenylvinyl-1-phosphonic acid is a compound readily accessible by reacting acetophenone with tetraphosphorus hexoxide (cf. DE-A-31 25 329) or phosphorus trichloride (cf. DE-A-33 23 392).

As described in Vysokomolekul, Soedin. 7 (12), 2160 (1965), 1-phenylvinyl-1-phosphonic acid is not homopolymerizable using a standard radical initiator.

In Izv. Vyssh. Uchebn. Zaved, Khim. Khim. Tekhnol. 22 (3) 360 (1979), it has however been described that 1-phenylvinyl-1-phosphonic acid can be polymerized in the presence of dicumyl peroxide at 125°–145° C. to give polyphosphonic acid.

We have now unexpectedly found that 1-phenyltetraline-1,4-diphosphonic acids are obtained in the form of a mixture of two diastereoisomers by heating 1-phenylvinyl-1-phosphonic acid to a temperature of from 120°–210° C., preferably 140°–190° C.

The mixture is easy to separate into its components by suspending the reaction product in water in which β-1-phenyltetraline-1,4-diphosphonic acid becomes dissolved and α-1-phenyltetraline-1,4-diphosphonic acid remaining behind as crystalline solid matter is separated from the solution obtained.

The aqueous solution of β-1-phenyltetraline-1,4-diphosphonic acid formed and separated can be evaporated and taken up in methanol with formation of a crystalline precipitate and β-1-phenyltetraline-1,4-diphosphonic acid is obtained by separating the crytalline precipitate from mother liquor.

It is naturally also possible for the procedure just described to be inversed. To this end, the reaction product is suspended in methanol in which α-1-phenyltetraline-1,4-diphosphonic acid becomes dissolved and β-1-phenyltetraline-1,4-diphosphonic acid remaining behind as crystalline solid matter is separated from the solution. α-1-phenyltetraline-1,4-diphosphonic acid is ultimately obtainable by evaporating the methanolic solution and taking it up in water.

The feed material used in this invention should generally be heated over a period of 1–30 hours, depending on the heating temperature selected.

1-phenyltetraline-1,4-diphosphonic acids are agents useful in the after-treatment of phosphatized metal surfaces.

The following Example illustrates the invention.

EXAMPLE 150 g 1-phenylvinyl-1-phosphonic acid was heated to 180° C. over a period of 6 hours. $^{31}$P-NMR spectroscopy indicated that the melt obtained consisted of two diastereoisomeric compounds, namely α-and β-1-phenyltetraline-1,4-diphosphonic acids in the isomeric ratio α:β=2:1. The product was taken up in 200 ml water and the solid matter was separated from the suspension.

88 g α-1-phenyltetraline-,4-diphosphonic acid was separated. ($^{31}$P-NMR-spectrum (methanol): AB-system with $\delta_{A}=27.4$ ppm, $\delta_{B}=26.9$ ppm, $J_{AB}=4$ hz). It was spectroscopically pure.

The concentrated mother liquor was taken up in methanol. 25 g spectroscopically pure β-1-phenyltetraline-1,4-diphosphonic acid crystallized out; it was filtered off ($^{31}$P-NMR-spectrum (methanol): AB-system with $\delta_{A}=26.8$ ppm, $\delta_{B}=26.3$ ppm $J_{AB}=3.0$ hz); the residual quantity of a mixture of the two isomers was in the mother liquor.

We claim:

1. 1-phenyl-tetraline-1,4-diphosphonic acids of the formula

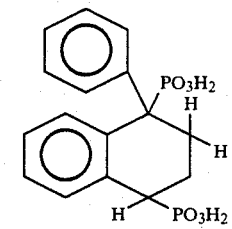

2. A process for making α- and β-1-phenyl-tetraline-1,4-diphosphonic acids which comprises heating 1-phenylvinyl-1-phosphonic acid to 120°–210° C. until the said diphosphonic acids are formed as reaction products; suspending those reaction products in water, in which β-1-phenyltetraline-1,4-diphosphonic acid becomes dissolved and α-1-phenyltetraline-1,4-diphosphonic acid remains behind as crystalline solid matter; and separating said crystaline solid matter from the solution thus obtained.

3. The process as claimed in claim 2, wherein the formation of said reaction products is effected at a temperature of from 140° to 190° C.

4. The process as claimed in claim 2, wherein the aqueous solution of β-1-phenyltetraline-1,4-diphosphonic acid formed and separated is evaporated, taken up in methanol with formation of a crystalline precipitate and β-1-phenyltetraline-1,4-diphosphonic acid is obtained by separating the crystalline precipitate from mother liquor.

5. A process for making α- and β-1-phenyltetraline-1,4-diphosphonic acids which comprises heating 1-phenylvinyl-1-phosphonic acid to 120°–210° C. until the said disphosphonic acids are formed as reaction products; suspending these reaction products in methanol, in which α-1-phenyltetraline-1,4-diphosphonic acid becomes dissolved and β-1-phenyltetraline-1,4-diphosphonic acid remains behind as crystalline solid matter; and separating said crystalline solid matter from the solution thus obtained.

* * * * *